US00PP22694P2

(12) United States Plant Patent
Hooper

(10) Patent No.: US PP22,694 P2
(45) Date of Patent: May 1, 2012

(54) ***MAGNOLIA* PLANT NAMED 'CLEOPATRA'**

(50) Latin Name: *Magnolia soulangeana*
Varietal Denomination: Cleopatra

(76) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 12/806,096

(22) Filed: Aug. 5, 2010

(51) Int. Cl.
*A01H 5/00* (2006.01)

(52) U.S. Cl. ..... Plt./223

(58) Field of Classification Search ..... Plt./223
See application file for complete search history.

*Primary Examiner* — Susan McCormick Ewoldt
(74) *Attorney, Agent, or Firm* — Mark Bourgeois

(57) ABSTRACT

A new cultivar of *Magnolia* plant named 'Cleopatra' that is characterized by purple flowers, an upright habit and flowering during the first year of growth.

1 Drawing Sheet

Botanical classification: *Magnolia soulangeana.*
Variety denomination: 'Cleopatra'.

BACKGROUND OF THE INVENTION

The present invention relates to a new and distinct cultivar of *Magnolia* plant botanically known as *Magnolia soulangeana* and hereinafter referred to by the cultivar name 'Cleopatra'.

The new cultivar is the product of a breeding program conducted by the inventor in a cultivated area of Waitara, New Zealand. The objective of the breeding program is to develop new *Magnolia* cultivars that have unusual flower colors.

'Cleopatra' is a hybrid that originated from the female or seed parent *Magnolia soulangeana* 'Sweet Simplicity' (not patented) and the male or pollen parent *Magnolia soulangeana* 'Black Tulip' (not patented). The crossing was conducted in 1998. The cultivar 'Cleopatra' was selected by the inventor in 2003 as a single plant within the progeny of the stated cross in Waitara, New Zealand.

Asexual reproduction of the new cultivar 'Cleopatra' by budding was first performed in 2004 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'Cleopatra'. These traits in combination distinguish 'Cleopatra' as a new and distinct cultivar.

1. *Magnolia* 'Cleopatra' exhibits purple flowers.
2. *Magnolia* 'Cleopatra' exhibits an upright habit.
3. *Magnolia* 'Cleopatra' exhibits flowers during the first year of growth.

The closest comparison varieties are *Magnolia* 'Royal Purple' (not patented) and 'Lanarth' (not patented).

'Cleopatra' is different than 'Royal Purple' in having more rounded flowers, ovate shaped leaves, a more upright habit and earlier flowering.

'Cleopatra' is different than 'Lanarth' in having rounded bowl shaped flowers, ovate shaped leaves, a more upright habit and earlier flowering.

In comparison to the parent plants, 'Cleopatra' is different than the female parent 'Sweet Simplicity' in having a more upright habit, larger diameter branches and purple flowers. The flowers of 'Sweet Simplicity' have a white center.

'Cleopatra' is different than the male parent 'Black Tulip' in having a more upright habit, thinner diameter branches and purple flowers. The flowers of 'Black Tulip' are purple-red.

BRIEF DESCRIPTION OF THE DRAWING

The accompanying photograph illustrates the distinguishing traits of *Magnolia* 'Cleopatra'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'Cleopatra'. Data was collected in Waitara, New Zealand from 12 month old field grown plants. The time of year was Autumn and the average temperature was 18 to 25° Centigrade during the day and 6 to 12° Centigrade at night. Color determinations are in accordance with The Royal Horticultural Society Colour Chart 2001 edition, except where general color terms of ordinary dictionary significance are used. The growing requirements are similar to the species. 'Cleopatra' has not been tested under all possible conditions and phenotypic differences may be observed with variations in environmental, climatic, and cultural conditions, however, without any variance in genotype.

Botanical classification: *Magnolia soulangeana* 'Cleopatra'.
Use: Ornamental Tree.
Parentage: 'Cleopatra' is a hybrid of the female or seed parent *Magnolia soulangeana* 'Sweet Simplicity' and the male or pollen parent *Magnolia soulangeana* 'Black Tulip'.
Vigor: Moderately strong
Growth rate: 1 meter per year in young plants, 30 cm. per year in mature plants.

Growth habit: Upright.
Plant shape: Broad columnar.
Height: Average 1.8 m. in height.
Width: Average 70 cm. in width.
Hardiness: −18° to 40° C.
Propagation: Softwood cuttings and field budding.
Crop time: 2 years.
Stem:
- *Branching habit.*—Primary branching upward with shorter secondary branching.
- *Number of lateral branches.*—2 to 5.
- *Lateral branch diameter.*—7 to 10 mm. in diameter.
- *Lateral branch length.*—15 to 60 cm. in length.
- *Lateral branch strength.*—Moderately strong.
- *Stem color.*—Immature stems 146A to 146B, mature stems N200.
- *Pubescence.*—Short hairs present on young branches.
- *Internode length.*—5 to 10 cm. between nodes.
- *Shape.*—Round.
- *Surface.*—Smooth.
- *Stem strength.*—Moderately strong.
- *Lenticles.*—1 to 2 mm. in length, color 156C.

Foliage:
- *Texture.*—Slightly leathery.
- *Leaf arrangement.*—Alternate.
- *Compound or single.*—Single.
- *Quantity of leaves per lateral branch.*—5 to 10.
- *Leaf shape.*—Ovate.
- *Leaf apex.*—Acute.
- *Leaf base.*—Cuneate.
- *Leaf length.*—12 to 18 cm. in length.
- *Leaf width.*—6 to 10 cm. in width.
- *Pubescence.*—Present on undersides of leaves only.
- *Leaf margin.*—Entire.
- *Vein pattern.*—Reticulate.
- *Young leaf color* (*upper surface*).—144A suffused with 200A.
- *Young leaf color* (*lower surface*).—147A to 147B.
- *Mature leaf color* (*upper surface*).—147A.
- *Mature leaf color* (*lower surface*).—N137B.
- *Vein color* (*lower surface*).—146A.
- *Vein color* (*upper surface*).—146B to 146C.
- *Leaf attachment.*—Petiolate.
- *Petiole dimensions.*—1.7 cm. in length, 3 mm. in width.
- *Petiole color.*—147A suffused with 200A.
- *Durability of foliage to stress.*—High.

Flower:
- *Flower arrangement.*—Bowl shaped flowers held upright.
- *Quantity of flowers per lateral stem.*—1.
- *Quantity of flower buds per lateral stem.*—1.
- *Quantity of flowers and buds per plant.*—Approximately 5.
- *Flowering season.*—Spring to Summer.
- *Time to flower or response time.*—6 to 8 weeks after breaking dormancy.
- *Fragrance.*—Yes.
- *Self-cleaning or persistent.*—Self cleaning.
- *Flower bud length.*—30 mm. in length.
- *Flower bud diameter.*—13 mm, in diameter.
- *Flower bud shape.*—Ovate.
- *Rate of bud opening.*—14 days.
- *Bud color.*—71A.
- *Flower aspect.*—Upright.
- *Flower shape.*—Bowl shaped.
- *Flower dimensions.*—13 cm. in diameter and 9 cm. in height.
- *Flower longevity.*—Lasts approximately 4 to 6 days on plant.
- *Tepal texture.*—Glabrous.
- *Tepal arrangement.*—Whorled.
- *Number of tepals.*—9 to 12 in number.
- *Fused or unfused.*—Not fused.
- *Tepal shape.*—Obovate.
- *Tepal margin.*—Entire.
- *Tepal apex.*—Acute.
- *Tepal base.*—Rounded.
- *Tepal dimensions.*—9 cm. in length and 7 cm. in width.
- *Tepal color when opening* (*upper side*).—71A.
- *Tepal color when opening* (*under side*).—71A.
- *Tepal color when fully opened* (*upper side*).—71A with 71C at base.
- *Tepal color when fully opened* (*under side*).—71A.
- *Tepal color fading to.*—71D.

Peduncle:
- *Peduncle dimensions.*—4 mm. in length and 10 mm. in diameter.
- *Peduncle angle.*—Vertical.
- *Peduncle color.*—146C.

Reproduction organs:
- *Stamen number.*—60 to 80.
- *Anther shape.*—Curved.
- *Anther length.*—18 mm. in length.
- *Anther color.*—Pink with purple base and tips.
- *Pistil number.*—1 in number.
- *Stigma shape.*—Round.
- *Stigma color.*—Pink.
- *Ovary.*—Ovaries grouped into a column 18 to 25 mm. in length.

Fruit:
- *Shape.*—Cone.
- *Quantity.*—4 to 6 cones.
- *Dimensions.*—10 cm. in length and 3 cm. in diameter.
- *Texture.*—Smooth with raised lenticels.
- *Color.*—138B, turning 46C when ripe.

Seed:
- *Quantity.*—2 seeds per ovary.
- *Seed dimensions.*—11 mm. in length and 9 mm. in diameter.
- *Seed color.*—202A.
- *Disease and pest resistance.*—Plants of the new *Magnolia* have not been observed for disease or pest resistance.

I claim:

1. A new and distinct variety of *Magnolia* plant named 'Cleopatra' as described and illustrated.

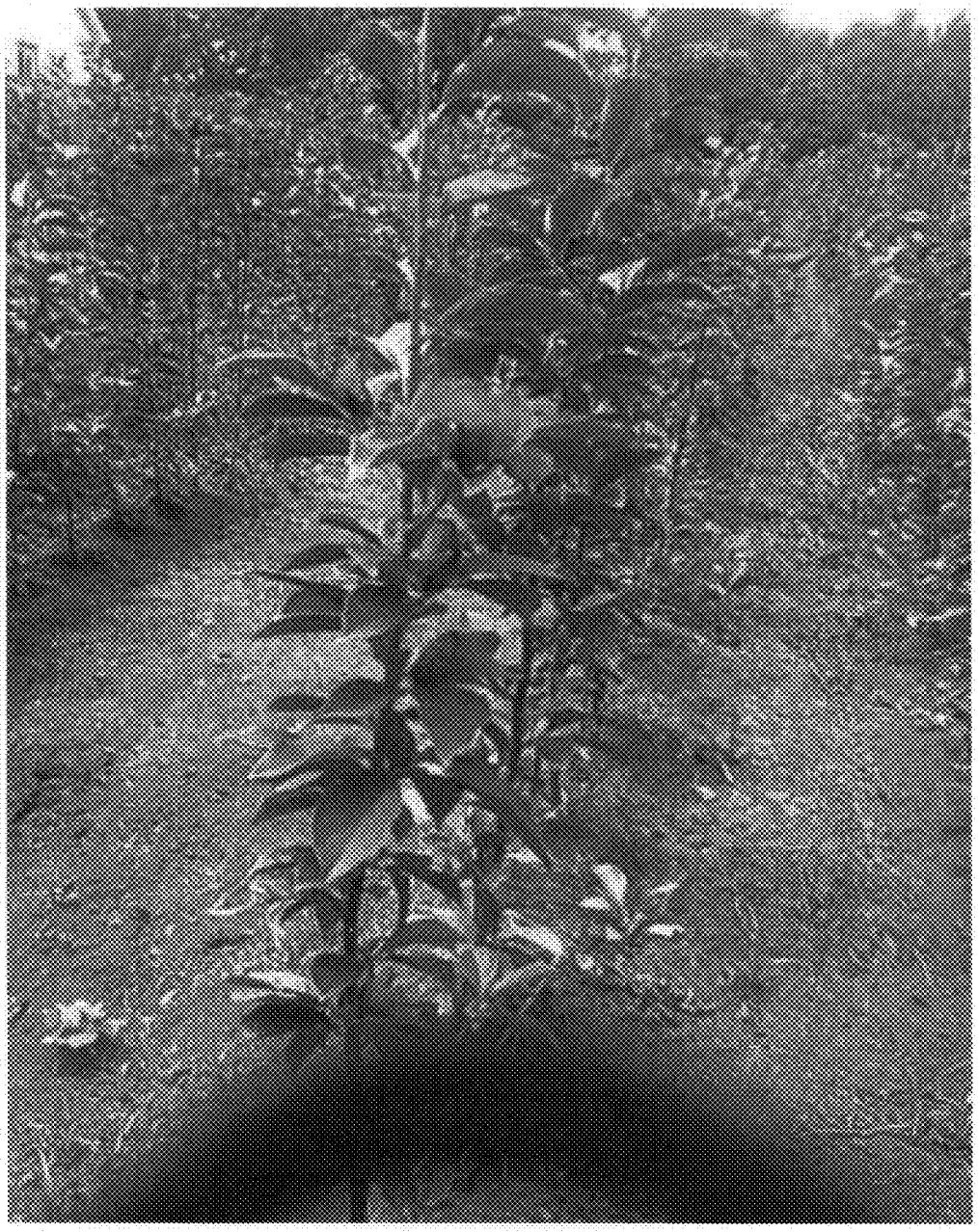

* * * * *